United States Patent [19]

Meline et al.

[11] Patent Number: 4,537,082
[45] Date of Patent: Aug. 27, 1985

[54] REFERENCE FRAME AND HOLD-DOWN SUPPORT SYSTEM FOR REMOTE SUPPORTED AXIAL TORSIONAL EXTENSOMETER

[75] Inventors: Harry R. Meline, Minnetonka; Richard A. Meyer, Carver, both of Minn.

[73] Assignee: MTS Systems Corporation, Eden Prairie, Minn.

[21] Appl. No.: 573,821

[22] Filed: Jan. 24, 1984

[51] Int. Cl.³ ............................................. G01N 3/02
[52] U.S. Cl. ................................... 73/794; 33/148 D
[58] Field of Search ................. 73/794, 796, 826, 831, 73/837, 847; 33/143 L, 147 D, 148 D, DIG. 13

[56] References Cited

U.S. PATENT DOCUMENTS

| | | | |
|---|---|---|---|
| 3,402,472 | 9/1968 | Riley | 73/763 X |
| 3,789,508 | 1/1974 | Meline | 33/148 |
| 4,160,325 | 7/1979 | De Nicola | 33/148 D |

OTHER PUBLICATIONS

Product Specification, MTS Systems Corporation, Model Series 632.50 and 635.51, High Temperature Axial Extensometers, 1980.

Primary Examiner—Jerry W. Myracle
Attorney, Agent, or Firm—Kinney & Lange, P.A.

[57] ABSTRACT

A support system provides a stable reference frame to support an extensometer assembly that measures both axial and torsional strains in a specimen. The reference frame is made so that it will retain an optimal relationship between the specimen and the test machine which is used for loading the specimen. The reference frame is made so that it will not substantially change position in relationship to the specimen during the specimen loading, or cross talk from one measurement axis to the other, while accommodating load frame deflections during the application of axial and torsional loads on the specimen.

16 Claims, 7 Drawing Figures

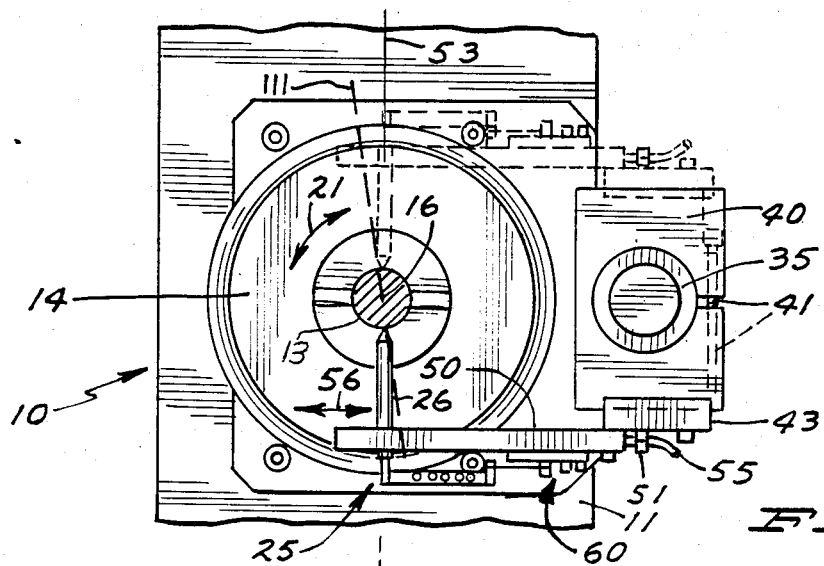
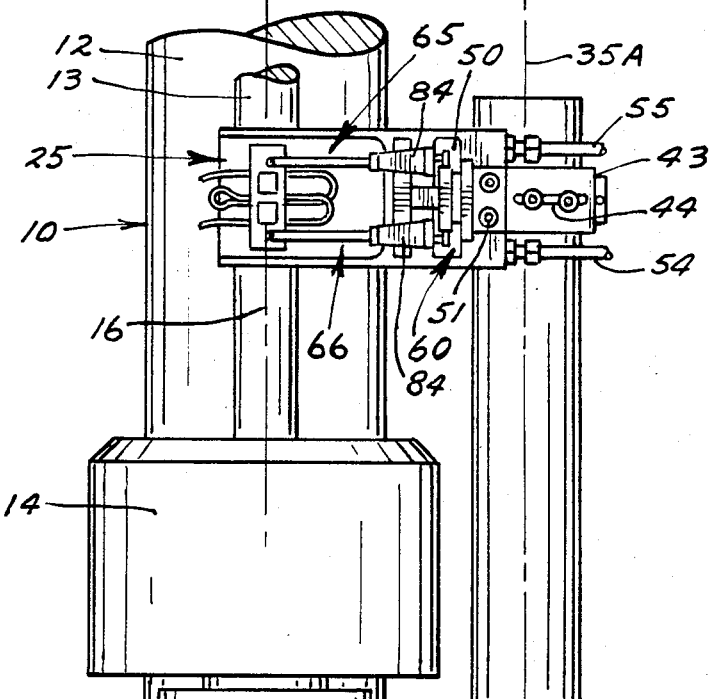
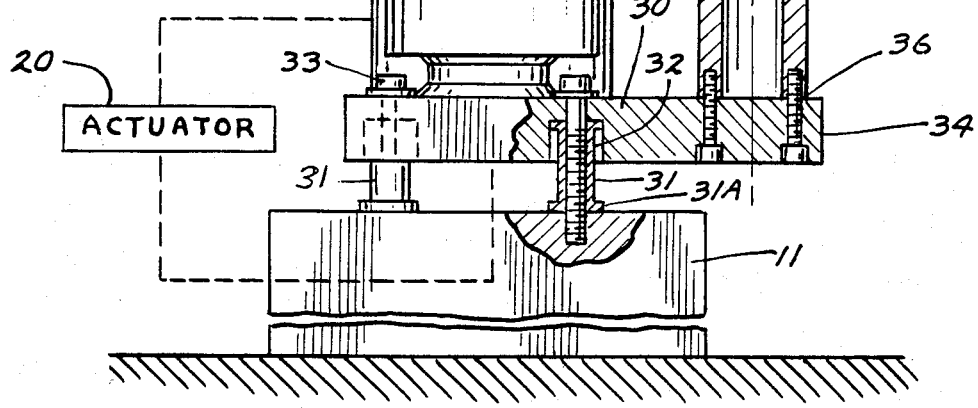

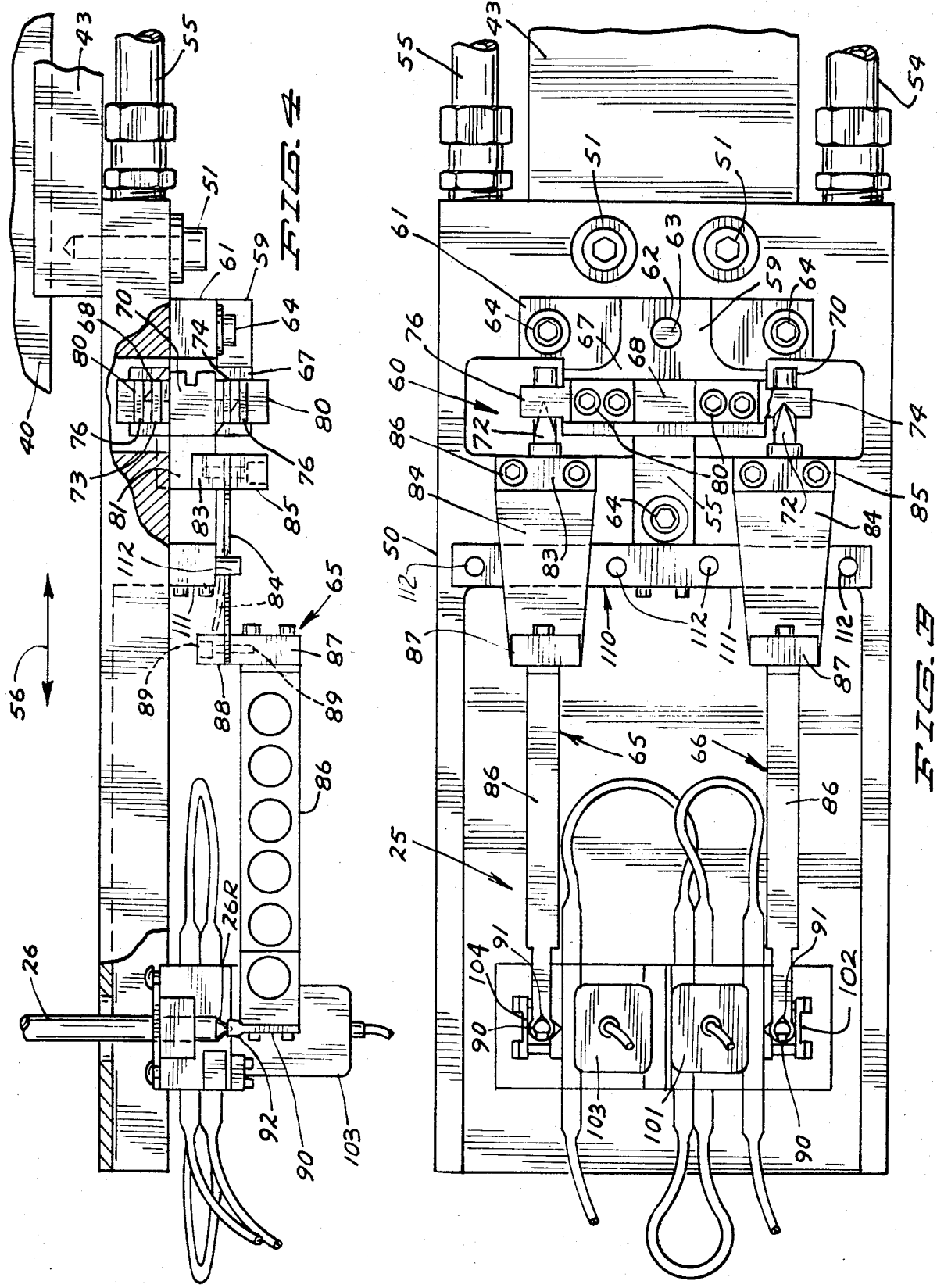

4,537,082

REFERENCE FRAME AND HOLD-DOWN SUPPORT SYSTEM FOR REMOTE SUPPORTED AXIAL TORSIONAL EXTENSOMETER

BACKGROUND OF THE INVENTION

1. Field of the Invention

The present invention relates to a support system to support extensometers remotely from the specimen and which provides a stable reference support during times when the specimen is subjected to both axial and torsional loads.

2. Description of the Prior Art

Remotely supported extensometers have been used for various applications, including high temperature applications where a shield is interposed between the extensometer and a heated specimen. The hold-down force of such extensometer is reacted to the heat shield and then to the column or support of the load frame that is used for loading the specimens. Devices of the general type are shown in Product Specification 632.50/0.51 of MTS Systems Corporation, Eden Prairie, Minn., the assignee of the present application, showing high temperature axial extensometers forming prior art devices.

The mounting of the extensometer becomes more complex when an arrangement of extensometers is used for measuring both axial and torsional strains of a specimen.

The need for adjustments in various degrees of freedom is also present when both axial and torsional strains are being measured, and the mounting arrangement has to accommodate the various adjustment movements independently of the design of the extensometers themselves.

SUMMARY OF THE INVENTION

The present invention relates to a support and hold-down system for providing a reference frame that will hold high temperature extensometers independently of the specimen in proper orientation when the specimen is being subjected to both axial and torsional strains. High temperature extensometers require use of elongated rods, with first ends of the rods engaging the specimen and the second opposite ends pivotally supported on the support and hold-down system. As the specimen is loaded the ends of the rods in contact with the specimen will spread and twist as they pivot about their second ends. The support and hold-down system provides a spring force which loads the rods against the specimen and which is rigid in the necessary axes to insure that the pivot points of the second ends of the rods and the specimen axis define a plane all during the specimen testing.

The support system is supported on the base for the load frame used for loading the specimen. The support system is stiff in the axes necessary for obtaining accurate measurements of strain sensed by the supported extensometer assembly.

Adjustability in the necessary degrees of freedom is also provided so that the support may be adjusted for different configurations of specimens and test load frames.

BRIEF DESCRIPTION OF THE DRAWINGS

FIG. 1 is a side elevational view of a support system made according to the present invention with the test load frame used for loading a specimen shown fragmentarily;

FIG. 2 is a top plan view of the support system of FIG. 1;

FIG. 3 is an enlarged side elevational view of a support showing the extensometers used on the outside of a heat shield;

FIG. 4 is a top plan view of the device of FIG. 3;

DETAILED DESCRIPTION OF THE PREFERRED EMBODIMENTS

Figure 5:
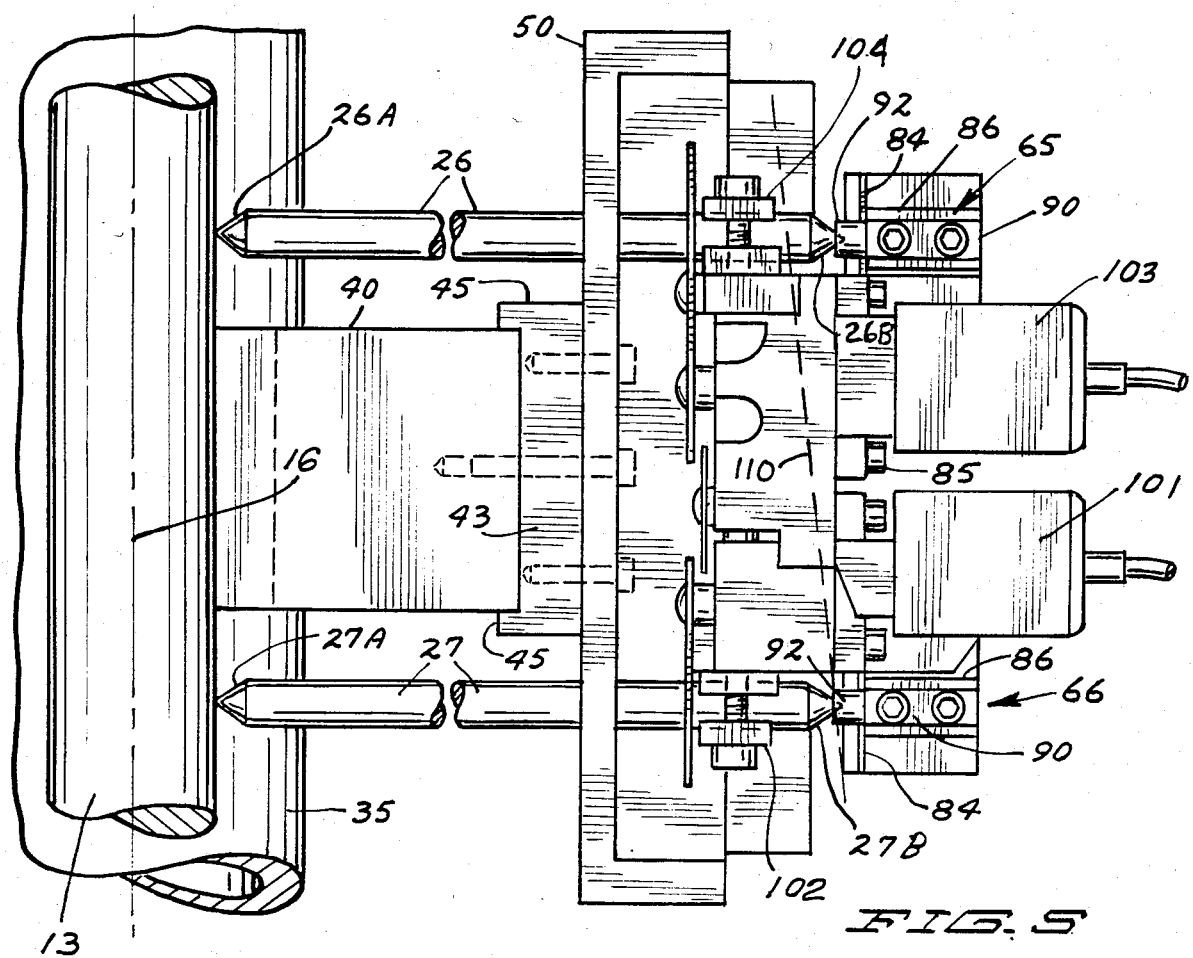
FIG. 5 is an end view showing a specimen with extensometer contact rods coming from the support system and showing portions of the support system fragmentarily.

In FIG. 1, a specimen test frame indicated generally at 10 is shown only fragmentarily, and is of the usual type that includes a base 11, and a pair of upright columns on opposite ends of the base. One of the columns is shown at 12, and is fixed to the base. In usage, the upper ends of the two columns 12 support a cross head (not shown) that extends between the columns and on which a specimen grip is used for gripping an upper end of a specimen indicated at 13 that is to be tested.

The lower end of specimen 13, as shown, is supported in a grip 14 of conventional design that includes a coupling 15 below the grip for measuring the axial loads, and in this case is provided with an actuator for not only loading the specimen in tension, that is along the central axis 16, 16 of the specimen 13, but also to load the specimen in torsion. In other words, the grip 14 can be rotated (a few degrees during test) about the axis 16 in order to load the specimen 13 as desired. The actuator is shown schematically at 20, and includes means for rotational (torsional) and axial loading.

When the actuator 20 is operated, the specimen 13 may be loaded in tension or compression, that is in directions along the axis 16, and also may be loaded in torsion or in other words twisted about the axis 16. The torsional loading directions are indicated by the double arrow 21 in FIG. 2.

In order to measure the strain in specimen 13, an extensometer assembly indicated generally at 25 is supported independently of the specimen in this instance. The extensometer assembly 25 can be of any conventional design, but in the preferred form a pair of conventional extensometers are connected together so that one of the extensometers will measure movements along the axis 16, between two rods which contact the specimen. These rods, in the form shown, where high temperature testing is desired, comprise quartz rods 26 and 27 (see FIG. 5) that have outer ends shown at 26A and 27A, respectively, that engage the specimen 13 in desired locations. Small dimples may be provided the specimen for the quartz rod ends to insure that the rods do not slip, and relative movement between the rod 27 and the rod 26 in the directions as indicated by the arrow 21 (torsion) is measured by a separate extensometer forming part of the assembly 25. The particular form of extensometer assembly used is not a part of the present invention.

Support for the rods 26 and 27 and the extensometer assembly 25 is provided by a support frame designed to insure adequate rigidity in required directions, while minimizing the transfer of bending or deflection of the test frame to the extensometers, which would affect the measurements to be made.

As shown in FIG. 1, a support plate 30 forms the main portion of the reference frame, and it is attached to the base 11 of the test frame in a manner that will isolate the reference frame and the the support plate 30 from bending or twisting movements of the test frame base plate 11 under normal loading. When the specimen is loaded along the axis 16, the base 11 of the test frame will tend to bend between the columns 12 because of reaction of loads between the actuator 20 and the upper crosshead of the test frame. This bending movement of the test frame is to be isolated from the support for the extensometers.

As shown, the support plate 30 has a center opening therethrough, through which the loading links between the coupling 15 and actuator 20 will pass. The plate 30 extends on both sides of the central axis 16 in directions between the columns of the load frame as can be seen in FIG. 2. A plurality of stand-off flexure supports indicated at 31, symmetrically located about the central axis 16 of the specimen are used to couple plate 30 to the base 11. The plane of plate 30 is perpendicular to the axis 16, as shown.

The stand-off supports 31 are spool type members having end flanges 31A of suitable size and a central connecting tubular section. One flange 31A of each support is supported on the upper surface of the base 11 of the test frame, and the opposite end of each support is supported on an inner surface of a separate recess opening 32 formed for each of the stand-off supports in the support plate 30. As shown, there are four such stand-off supports 31 that are used to space the plate 30 upwardly from the upper surface of the test frame base 11 and are made to flex, to provide flexural movement between the test frame base 11 and the support plate 30.

The support plate 30 is held on the stand-off flexure supports by cap screws 33 that pass through provided openings in the support plate 30 and through the central opening of stand-off flexure supports 31. The cap screws 33 are tightened down to compress the supports 31 so that there is no tendency of the end flanges 31A to creep or fret when loaded.

The support plate 30 therefore surrounds the axis of the specimen and extends laterally therefrom to one side of the specimen. The support plate 30 has an end portion that extends in a direction away from and perpendicular to a plane through the axis 16 and through the axes of the columns 12 of the test frame. As shown, the support plate 30 end portion forms a neck portion 34 to one side of the test frame. An upright tubular support column 35 is mounted on the upper surface of neck 34 with suitable cap screws indicated at 36. A sufficient number of cap screws 36 are used so that the support column is rigidly supported. For example, eight such cap screws normally would be threaded into the lower end of the tubular column 35 to form a very secure connection that is rigid, and which has a high natural frequency. The column 35 is of sufficient length to extend up into the mid-range of the specimen 13 as shown in FIG. 1, and must be sufficiently long to permit supporting the extensometer assembly 25 in a region on the specimen that is of interest for testing.

At the upper end of the column 35 a column clamp 40 is mounted. The column clamp 40 is a split clamp, and has an opening that receives the column 35, and a cap screw indicated at 41 spans the clamping split. The cap screw 41 will permit the clamp 40 to be firmly clamped on the column against rotational and axial movement relative to the column 35 upon tightening of this cap screw. The cap screw 41 threads into one side of the block 40, and the cap screw head is recessed into block on the other side of the split as shown in dotted lines. The block 40 can be adjusted rotationally about the axis of the column 35, as well as longitudinally along the column 35, and then clamped into place. It can be adjusted for proper alignment of the extensometer assembly 25 with the specimen as well.

As can perhaps best be seen in FIG. 5, the block 40 has outer end edges over which a slider clamp 43 may be mounted. The slider clamp 43 has an elongated slot 44 along its base member, as shown in FIG. 1, and is shaped like a shallow channel which has longitudinally extending, relatively short legs 45 on the upper and lower edges thereof that fit over the edges of the block 40 as shown in FIG. 5. The clamp 43 can thus be slid along the block in direction perpendicular to the axis 35A of the column 35 (axis 35A is shown in FIG. 1 and is parallel to the axis 16 of the specimen 13). The clamp 43 can be moved at least a limited amount along the end of block 40 for adjustment of the clamp 43 inwardly and outwardly or in other words, in directions toward and away from the specimen 13. In FIG. 2 it can be seen that the end of the block 40, where the clamp 43 is mounted, is spaced laterally outward from the specimen 13 as well. The clamp is positioned to a side of the specimen.

As part of the support system forming a reference frame for the extensometer assembly 25, a heat shield-support plate indicated at 50 is clamped with suitable cap screws 51 to one end of the clamp 43. The heat shield is of size to extend alongside the specimen as perhaps best seen in FIG. 2. The adjustment of the clamp 43 along clamp 40 and along the slot 44 also permit moving the heat shield plate 50 in and out transverse to the axis 16 of the specimen. As shown the heat shield plate 50 does extend laterally to the specimen. The plate 50 is spaced from the specimen. The outer end of the heat shield plate 50 extends beyond the plane that is defined by the central axes of the column 12 and passing through this axis 16 of the specimen. This plane is shown at 53 in FIG. 2 for reference purposes, and it can be seen that the heat shield extends to the opposite side of this plane 53 from the column 35.

The heat shield plate 50 is a support plate that is relatively rigid, and is shown with some detail in FIGS. 3 and 4.

In the form shown, the heat shield plate 50 has liquid passages in it for cooling, and has conduits shown at 54 and 55 for providing inlet and outflow of liquid coolant. The heat shield may be air cooled if desired, or can be other desired configurations.

The heat shield plate 50 is firmly clamped onto the clamp member 43 in a desired location, and adjustments of the plate 50 relative to the specimen in directions as indicated by the double arrow 56 in FIGS. 2 and 4 can be made by loosening the cap screws holding the clamp 43 in place and adjusting the clamp and thus plate 50 along the slots 44 before retightening the cap screws.

A support bracket assembly that is used for mounting the rods 26 and 27 in position and permitting them to move in response to tension and torsional stresses in the specimen 16 is indicated generally at 60. This is mounted to the heat shield plate 50 in the form shown, and the heat shield forms a mounting means for providing stability in the overall support bracket assembly.

The bracket assembly 60 includes a bracket base 61 that has a central boss 59 that has an opening 62 therein. The opening 62 closely fits over a dowel pin 63. The dowel pin 63 in turn is fixedly supported to the heat shield plate 50. The bracket 67 can be moved about the dowel pin 63, and is held in place with suitable cap screws 64 on upper, lower and central forwardly extending ear members of the bracket 61. The cap screws 64 fit through oversize holes in the ear members of bracket 61 to that some tilting adjustment about the axis of the pin 63 can be made for adjustment purposes. This of course, as will be noted, will provide the capability to substantially change the orientation of the extensometer assembly 25 that supports the rods 26 and 27 for alignment and adjustment. The cap screws 64 can be fastened securely in place to hold the bracket base clamped to the heat shield plate 50 very securely once it has been aligned.

The base 61 provides a support for a pair of arm assemblies indicated generally at 65 and 66 which are essentially identical, and which are attached to the base 61 through "knife" edges that permit the arm assemblies to pivot individually about generally parallel axes that are perpendicular to the axis of the specimen and extend normal to the plane of the heat shield plate 50. The arm assemblies 65 and 66 are substantially identically constructed, and a typical mounting for each arm assembly is shown in FIGS. 3, 4, 6 and 7.

The boss 59 of bracket 61 joins an upright mounting center block portion 67. The mounting block portion 67 has a vertically extending guideway or groove 68 defined on each side thereof. The grooves or guideways 68 extend throughout the full vertical length of the block portion 67 and at the upper and lower ends of the guide ways there are a plurality of retainer clips that are fastened in place to hold knife edge arm supports at both the bottom and top of the mounting block portion 67 of base 61.

Figure 6:
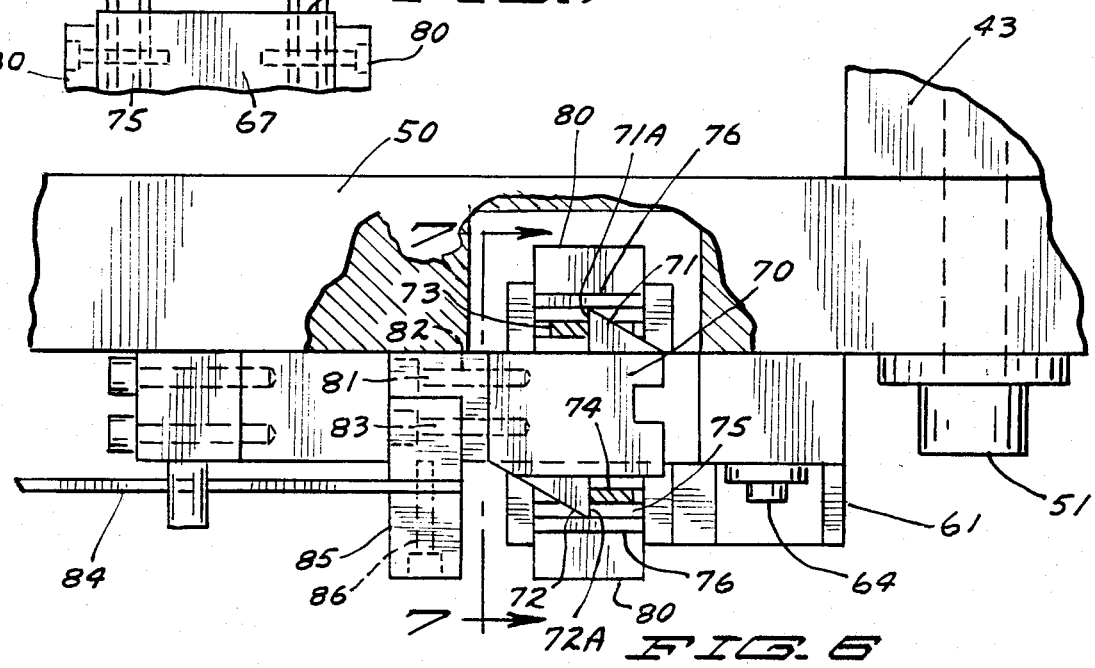
FIG. 6 is an enlarged top view showing a typical support for one of the pivoting arms of the support.

The upper arm assembly is shown in FIG. 6. An arm base block 70 has a first knife edge member 71 extending laterally out from one side thereof and a second knife edge member 72 extending out from the opposite side. The knife edge members 71 and 72 are integrally formed with the block 70. The knife edge member 71 has a knife edge 71A facing in direction toward the remote end of the arm (where the extensometers are located). The knife edge 71A fits into a recess or notch in an upright, flat clip 73 that is held in the recess 68 on the corresponding side of the block portion 67.

Figure 7:
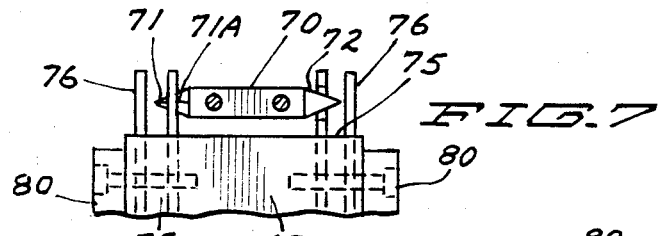
FIG. 7 is a sectional view taken on line 7—7 in FIG. 6.

The knife edge member 72 has a knife edge 72A which fits in a recess or notch in an upright clip 74 portioned in the recess 68 on the opposite side of the block portion 67 from the clip 73. The knife edge 72A faces in direction away from the remote end of the arm so that the knife edges 71A and 72A face in opposite directions. A suitable spacer 75 is used on the outer sides of each of the clips 72 and 73, and then a separate stop clip 76 is stacked or positioned to the outside of each of the spacers 75. The stop clips 76 as can be seen in FIG. 7 in particular, form a blocking wall to limit the movement of the arm base block 70 in the directions of extension of the knife edges. The clips 73, 74 and 76 and the spacers 75 are all held in place with clamp blocks 80, and suitable cap screws that are screwed into the block 67.

Thus the base portion for the arms 65 and 66 are made so that they will pivot on the knife edges 71A and 72A (which form a common axis) with respect to the clips 73 and 74. The clips 73 and 74 have the notches, as shown in FIG. 3 for the lower arm 66, that provide this pivoting or rocking movement of the knife edges.

Each of the arm assemblies 65 and 66 is in turn mounted through a suitable adapter block assembly 81 to its respective arm base 70 (see FIG. 6). The adapter block 81 includes a member that is bolted directly to the arm base 70 with cap screws 82, and an uprightly extending second block portion 83 is fastened in place to the block 81 and is held securely with respect to the arm base 70.

The block portion 83 is used to clamp and hold a spring arm blade 84 to the arm base so that the side surfaces of the blade extend up and down as shown in FIG. 3. The spring arm blades 84 are held in place on the adapter block 83 with a clamp block 85 that is held in place with suitable cap screws.

The blades 84 are spring material, and at rest are bent or curved so that they bend inwardly toward the heat shield plate 50 generally as shown in dotted lines in FIG. 4. When the arm assemblies are in place and the contact rods 26 and 27 are in place against the specimen, the spring blades 84 are generally planar or flat as shown in solid lines in FIGS. 4 and 6.

As mentioned, there are upper and lower arm assemblies 65 and 66, and both arm assemblies are identical in construction. The arm blade members 84, as shown, taper in height from a vertical height maximum at the end where they are clamped with the clamp blocks 85, to a narrower vertical height at the end closer to the specimen as shown in FIG. 3. The axial length of the blade members 84 and their size depends in part on the spring load that is desired for holding the contact rods 26 and 27 against the specimen. At the outer or remote end of each blade member 84 an arm extension 86 is attached through a block member 87 and a clamp 88 to clamp the end of the blade members 84. The block and clamp are held together with cap screws 89. The arm extensions 86 are very lightweight, and extend toward the specimen a desired distance so that the size of the arm assembly is within the desired parameters. At the outer end of each of the arm extensions 86 there is a contact rod support 90 attached thereto. This includes a cylindrical shank with one flat surface, as can be seen in FIG. 3, and the cylindrical shank fits within a V notch indicated at 91, formed at the end of each arm extension. The notches 91 extend laterally across the end of the arm extensions 86. An outer head member 92 is formed on each of the shanks of each support 90 and each head member 92 has an inner conical bore or recess that receives a cone point 26B and 27B, respectively, on the contact rods 26 and 27. The points 26B and 27B form pivot points at the outer ends of the arms for the rods 26 and 27. The pivot points are for universal pivoting held coupled by the spring load of the arms.

The contact rods 26 and 27 are loaded under compression through the members 90 in direction toward the specimen 13, under the spring loading of the spring arm blade members 84.

The relative movement of the ends 26A and 27A of the contact rods 26 and 27 is measured by the extensometer assembly 25. The outer ends 26A and 27A will tend to separate under tension loads on the specimen 13, and this will be measured by an extensometer 101 that has one arm clamped to the lower contact rod 27 with a suitable clamp 102, and the other arm of the extensometer 101 is connected to a second extensometer 103 which is oriented to measure torsional strains occurring at 90° to the first extensometer and which has its other arm connected to an upper contact rod 26 with a suitable clamp 104. The extensometer arrangement can be through any desired type of connection, but the second extensometer 103 is oriented so that it will measure the torsional strain on the specimen 13 when the ends 26A and 27A tend to move relative to each other in a rotational direction about axis of the specimen.

The exact configuration of the extensometers 101 and 103 for sensing these movements does not form part of this invention. Each extensometer used may be similar to that disclosed in U.S. Pat. No. 3,789,508 made in a suitable size. The rods 26 and 27 are coupled to extensometers which will measure axial movement of the points 26A and 27A and also the torsional movement of these points relative to each other. To minimize "cross talk" pivot axes of the arms of the extensometers should be close to or substantially coincidental with the axis passing through the pivot points of the rods 26 and 27 at the points 26B and 27B.

The support arm assemblies 65 and 66, the attachment of arms 65 and 66 to the heat shield plate and to the base of the test frame machine, however, is very rigid in the directions needed to react the strain measurement. The spring arm blades 84 will exert the necessary inward force to keep the points 26A and 27A in contact with the specimen 13.

As the base 11 of the test frame tends to twist or bend, the flexure supports or standoffs 31 will elastically deform to accomodate the normal deflection, such as bending that occurs under normal specimen loads without adding "cross talk" loading to the other components of the support system, which would affect the indications of the extensometers.

If the test frame base 11 twists under loading, the plate 30 will also twist, but because the column 35 is on the center line of the base 11 and plate 30, that is on the bisecting plane perpendicular to the plane 54, the column 35 will not deflect or move under this twisting movement. The flexure supports 31 are soft in bending and stiff axially, so that the twisting is transmitted to the plate 30, but the bending is not. The flexures are symmetrically located about the central axis of loading, to insure that this accommodation of twisting occurs.

Any tendency of the points at either end of the contact rods 26 and 27 to separate, or move in unison in direction of the axis 16 is permitted by the pivotal movement of the knife edge members 71 and 72 in the respective mounting clips. The flat spring blades 84 will also permit the arms 65 and 66 to twist about the longitudinal axes of the arms.

During testing, the specimen 13 will be subjected to tension, compression and torsion. The outer end points of the quartz rods, shown at 26A and 27A are engaged against the specimen 13 under the spring load from the spring arm blade members 84 which exert a sufficient force to insure good contact during the test. The outer end points 26A and 26B thus must be movable along the axis of the specimen as the specimen elongates or is compressed under load, and also the points 26A and 26B must move laterally relative to each other as the outer surface of the specimen twists about its longitudinal axis under torsional loading. These movements of the outer ends of the rods 26 and 27 are accommodated by the universal pivotal mounting at the points 26B and 27B at the ends of the support arm assemblies 65 and 66.

The entire support frame assembly, including the mounting base 61, the column 35, and the plate 30 are made to have a high natural frequency and thus to be very stiff in the necessary axes to insure that the pivot points between the rods 26 and 27 and arm assemblies 65 and 66 always define a line which lies on a plane with the axis 16 of the specimen. In other words, even though the outer points 26A and 27A of rods 26 and 27 shift and move relative to each other, and the extensometer assemblies 101 and 103 may shift and move relative to each other as the specimen is tested, the orientation of the pivot points at points 26B and 27B is such that they define a line lying on a plane with the axis 16 of the specimen 13 to insure that there are no extraneous readings. If one of the points 26B or 27B moves off the plane which is defined by the axis 16 and the other point 26B or 27B, there will be an erroneous reading sensed by the extensometers because this movement will cause one or both of the extensometers to deflect.

For example, as shown in FIG. 5 the line between points 26B and 27B, that is the actual pivot points defined in connection with the conical socket members 90, can tilt in the defined plane as illustrated (in exaggerated condition) by the dotted line 113. This may occur in testing, but the line through the pivot points must continue to define a plane with the axis 16 in order to obtain accurate measurements.

The plane defined by the line between the pivot points formed by conical points 26B and 27B and the axis 16 can rotate about the axis 16 without affecting readings. In an exaggerated view, the plane could rotate to a position shown by the dotted line 114 in FIG. 2, (which is greatly exaggerated) without significantly affecting the readings, but the two lines, that is the axis 16 and the line between the pivot points 26B and 27B must lie in a plane in order to make the readings accurate.

It should be noted that the arm assemblies 86 form a four bar linkage as shown in FIG. 3, between the pivots of the knife edges at the base ends of the arms and the pivots of the conical points 26b and 27B on members 90. The spring force from the spring arm blade members 84 tending to create a compressive force on the rods 26 continues to hold the rods in positive engagement with the specimen throughout their necessary movements for testing.

The mounting base 61 has a forward extending ear portion as mentioned, which is used for mounting an arm movement stop assembly indicated generally at 110 (FIG. 3). This stop assembly 110 includes an upright bar 111 fixed to the base 61. The bar 111 has outwardly extending pegs 112 at spaced locations. The pegs 112 are arranged with respect to the arm blade members 84 so as to prevent excessive pivotal movement of the arms about the knife edges. The bar 111 is attached to the end of the forwardly extending portion of base 61 through suitable cap screws to hold it securely in place.

The support thus gives a very rigid frame of reference for mounting the rods 26 and 27 and the extensometers to provide a stable support for measuring torsional and axial movement.

The dotted line representation in FIG. 2 of a heat shield plate and extensometer assembly is to illustrate an alternate location in which the extensometer assembly may be used.

Although the present invention has been described with reference to preferred embodiments, workers skilled in the art will recognize that changes may be made in form and detail without departing from the spirit and scope of the invention.

What is claimed is:

1. An extensometer support for use in combination with a test frame having a base, and having means for loading a test specimen along a specimen loading axis generally perpendicular to the base, and for loading said specimen for rotation about its specimen axis, the improvement comprising a support plate, an upright column fixed to said support plate and laterally offset from a specimen when the plate is installed on a base for a test frame holding a test specimen, a plurality of flexure standoff members for mounting the support plate relative to the base in a position spaced from said base and connected to the base only through said standoff members, means at the upper end of said column for supporting an extensometer in engagement with a specimen to be tested, said standoff members providing a flexible connection to the base which will not substantially deflect extensometer members supported relative to and operatively engaging a specimen as the base deflects during loading of the specimen.

2. The extensometer support of claim 1, wherein said plate is mounted on a surface of said base facing a specimen mounted in a test frame having such base, and wherein the plurality of flexure stand-off members are symmetrically located about the specimen loading axis.

3. The extensometer support of claim 1, wherein said column has an axis parallel to the loading axis, a clamp adjustably mounted on said column for adjustable movement rotationally about the axis of the column and vertically along the axis of the column, and means to releasably secure said clamp in position on said column.

4. The extensometer support of claim 3 wherein said clamp comprises a block member having an end, a slider support mounted on said block member and adjustably movably connected thereto whereby said slider support can be moved in a direction generally perpendicular to the axis of the column, and means to support an extensometer on said slider support.

5. The combination specified in claim 4 wherein said slider support comprises a mounting plate, a base support on said mounting plate, and a pair of arms pivotally mounted on said base support about axes that are generally perpendicular to the axis of said column and are between the axis of the column and the axis of the test specimen.

6. The apparatus as specified in claim 5 wherein said arms extend in a direction toward the test specimen and are laterally offset therefrom, said arms having means at the end thereof for supporting an extensometer assembly including elongated rods adapted to engage a side surface of said specimen for determining strains in said specimen.

7. The apparatus as specified in claim 6 wherein said arms comprise at least one section forming a flat spring, each of said arms being urged in a direction by said flat spring so that the outer ends thereof are urged toward the specimen, said elongated rods each being pivotally coupled to one of the arms at the second ends of the arms and loaded by said arms in compression against a specimen to be tested.

8. The apparatus of claim 7 wherein said support plate is planar and the column is tubular and when mounted together they have a stiffness sufficient to substantially prevent the pivot points of the pivotal coupling of the rods to their respective arms from shifting from a position wherein a line defined by the pivot points of the pivotal coupling and the axis of a specimen being tested define a plane.

9. The apparatus as specified in claim 5 wherein said slider support has a pivot pin mounted thereon, and said base support for said extensometer arms is adjustably mounted for movement about the axis of said pivot pin, the axis of said pivot pin being generally parallel to the axis of mounting of said arms.

10. The apparatus as specified in claim 5 wherein said arms are pivotally mounted to the base support through the use of knife edge pivot means, said knife edge pivot means comprising pivot members extending in opposite directions from a central axis of said arms and having knife edges aligning to define which are the pivot axis the knife edge members being supported in notched supports on opposite sides of each of the arms, the knife edges facing in opposite directions on the opposite sides of said arms to resist rotational movement of the arms about axes parallel to the specimen axis.

11. For use in connection with a test frame comprising a base and means for loading a test specimen along a specimen loading axis, said base extending generally perpendicular to said loading axis and having an upper surface on a side thereof adjacent to said specimen that is substantially perpendicular to said axis, and wherein said base includes means for loading said specimen in direction along said axis and also in torsion about the axis, the improvement comprising an extensometer support for supporting an extensometer relative to a test frame base independently of the specimen including a support plate, said support plate having a plane and generally parallel to the upper surface of said base, a plurality of flexure support spools comprising stand-off members spacing the plate from the upper surface of such base, means to load the plate in compression against first ends of the support spools and when second ends of the flexure support spools are forced against the upper surface of such base to permit flexing movement of such base relative to the support plate when the support plate is supported thereon, said support plate having an extension portion extending laterally from the specimen loading axis of a test frame on which it is mounted, a rigid tubular upright column mounted on said extension portion of said support plate and having a central axis generally parallel to such test specimen axis and extending in a direction away from a base on which the support plate is mounted, clamp means on said column for adjustable movement along and about the axis of said column, a second support plate, means to adjustably support the second support plate on said clamp means for movement in a direction perpendicular to the axis of said column, said second support plate having a plane that is generally parallel the axis of the column, and generally spans the distance between the column and a test specimen mounted on a test frame on which the first mentioned support plate is mounted, a block mounted on said second support plate and adjustable about an axis generally perpendicular to the plane of the second support plate, a pair of arms mounted on said block for pivotal movement individually about axes perpendicular to the plane of the second support plate and parallel to the axis of adjustment of said block, said arms extending outwardly from their pivotal mounting in a direction generally toward the test specimen loading axis, but being laterally offset therefrom, said arms including flat spring means prebent to urge the outer ends of said arms in a direction toward the axis of a test specimen being tested in a test frame on which the arms are mounted, said flat spring means being substantially planar when the arms are supporting an extensometer assembly against a specimen located centrally on such a test specimen axis.

12. The apparatus of claim 11 and means to support an extensometer assembly, including a pair of rods having first ends for engaging a specimen to be tested under compression loading from said arms, and second ends pivotally coupled to the arms, respectively, for movement about pivot points that permit universal pivotal movement, the first mentioned support plate, the column, the second support plate and said arms being oriented to provide a mounting for the rods sufficiently stiff to substantially prevent either of the pivot points from being displaced from a plane defined by the test specimen loading axis and the other pivot point.

13. An extensometer support for use in combination with a test frame having a base, and having means for loading a test specimen along a specimen loading axis generally perpendicular to the base, and for loading said specimen for rotation about its specimen axis, the improvement comprising a support plate, an upright column fixed to said support plate and laterally offset from a specimen when the plate is installed on a base for a test frame holding a test specimen, a plurality of flexure standoff members for mounting the support plate relative to the base in a position spaced from said base and connected to the base only through said standoff members, means at the upper end of said column for supporting an extensometer in engagement with a specimen to be tested, including a pair of arms pivotally mounted at first ends thereof about an axis perpendicular to the axis of the column and spaced apart in the direction of the longitudinal axis of the column, the arm axes being positioned adjacent the column, a pair of elongated rods having first ends for engaging a specimen and second ends, means for pivotally mounting second ends of the elongated rods to the respective arms at second ends of the arms when the elongated rods are engaging a specimen to be tested, said standoff members providing a flexible connection to the base which will not substantially deflect extensometer members supported relative to and operatively engaging a specimen as the base deflects during loading of the specimen, said plate and column being sufficiently stiff to prevent the line defined by the pivot points of the second ends of the elongated rods from becoming substantially displaced from a plane passing through one of the pivot points of the second ends of the arms and the axis of a specimen to be tested.

14. The extensometer support of claim 13 wherein said plate is mounted on a surface of said base facing a specimen mounted in a test frame having such base, and wherein the plurality of flexure stand-off members are symmetrically located about the specimen loading axis.

15. The apparatus as specified in claim 13 wherein said arms each comprise at least one section forming a flat spring, each of said arms being urged in a direction by said flat spring so that the outer ends thereof are resiliently loaded in direction to load the rods in compression against a specimen being tested.

16. The apparatus of claim 15 wherein the pivot mounting of the first ends of the arms are elongated to provide rigidity against movement of the second ends of said arms in directions toward and away from a specimen to be tested, and the means for pivotally mounting the second ends of the elongated rods to the second ends of the arms, respectively, comprise means to permit universal pivotal movement.

* * * * *